United States Patent
Leuthold et al.

(10) Patent No.: US 10,517,973 B2
(45) Date of Patent: Dec. 31, 2019

(54) METHOD FOR THE STERILIZATION OF CHROMATOGRAPHIC MATERIAL AND CHROMATOGRAPHIC MATERIAL STERILIZED ACCORDING TO SAID METHOD

(71) Applicant: Sartorius Stedim Biotech GmbH, Göttingen (DE)

(72) Inventors: Martin Leuthold, Göttingen (DE); Louis Villain, Hannover (DE); Florian Taft, Hannover (DE)

(73) Assignee: Sartorius Stedim Biotech GMBH, Goettingen (DE)

( * ) Notice: Subject to any disclaimer, the term of this patent is extended or adjusted under 35 U.S.C. 154(b) by 211 days.

(21) Appl. No.: 15/567,113

(22) PCT Filed: Mar. 8, 2016

(86) PCT No.: PCT/EP2016/000405
§ 371 (c)(1),
(2) Date: Oct. 17, 2017

(87) PCT Pub. No.: WO2016/169630
PCT Pub. Date: Oct. 27, 2016

(65) Prior Publication Data
US 2018/0161465 A1    Jun. 14, 2018

(30) Foreign Application Priority Data
Apr. 24, 2015  (DE) .................. 10 2015 005 244

(51) Int. Cl.
*A61L 2/00* (2006.01)
*G01N 23/00* (2006.01)
(Continued)

(52) U.S. Cl.
CPC .............. *A61L 2/081* (2013.01); *A61L 2/18* (2013.01); *B01D 15/20* (2013.01); *B01D 15/206* (2013.01)

(58) Field of Classification Search
CPC ........... A61L 2/00; A61L 2/0035; A61L 2/081
(Continued)

(56) References Cited

U.S. PATENT DOCUMENTS

| 2011/0064608 A1 | 3/2011 | Lee et al. |
| 2013/0062267 A1 | 3/2013 | Gebauer |

FOREIGN PATENT DOCUMENTS

| EP | 0672 424 | 9/1995 |
| WO | WO 2003/030949 | 4/2003 |

(Continued)

OTHER PUBLICATIONS

Grönberg et al, "A tool for increasing the lifetime of chromatography resins", mAbs vol. 3, issue 2, pp. 192-202, Mar./Apr. 2011, 2011 Landes Bioscience.
(Continued)

*Primary Examiner* — Monzer R Chorbaji
(74) *Attorney, Agent, or Firm* — McDonnell Boehnen Hulbert & Berghoff LLP

(57) ABSTRACT

The present invention relates to a method for sterilizing a chromatography material, more particularly microporous polymer membranes, to a chromatography material which has been sterilized by the method according to the invention, to the use of the chromatography material sterilized according to the invention for the chromatographic removal of contaminants from a fluid, and to a closed chromatographic filtration system comprising a chromatography material sterilized according to the invention.

16 Claims, 4 Drawing Sheets

Type 3 membrane adsorber

(51) Int. Cl.
*A61N 5/00* (2006.01)
*A61L 2/08* (2006.01)
*B01D 15/20* (2006.01)
*A61L 2/18* (2006.01)

(58) Field of Classification Search
USPC ............... 422/1, 22–24; 250/432 R, 453.11, 250/454.11, 455.11, 492.1
See application file for complete search history.

(56) References Cited

FOREIGN PATENT DOCUMENTS

| | | | |
|---|---|---|---|
| WO | WO 2004/009143 | 1/2004 | |
| WO | WO-2004009143 A1 * | 1/2004 | ............... A23C 3/07 |
| WO | WO 2011/076386 | 6/2011 | |
| WO | WO 2013/074668 | 5/2013 | |
| WO | WO 2013/180633 | 12/2013 | |
| WO | WO 2015/109146 | 7/2015 | |
| WO | WO 2015/109246 | 7/2015 | |

OTHER PUBLICATIONS

Buchalla et la., "Characterization of volatile radiolysis products in radiation-sterilized plastics by thermal desporption-gas chromatography-mass spectrometry: screening of six medical polymers", Radiation Physics and Chemistry 56 (1999) 353-367.

* cited by examiner

Type 1 membrane adsorber

Type 2 membrane adsorber

Type 3 membrane adsorber

METHOD FOR THE STERILIZATION OF CHROMATOGRAPHIC MATERIAL AND CHROMATOGRAPHIC MATERIAL STERILIZED ACCORDING TO SAID METHOD

FIELD OF THE INVENTION

The present invention relates to a method for sterilizing a chromatography material, more particularly microporous polymer membranes, to a chromatography material which has been sterilized by the method according to the invention, to the use of the chromatography material sterilized according to the invention for the chromatographic removal of contaminants from a fluid, and to a closed chromatographic filtration system comprising a chromatography material sterilized according to the invention.

BACKGROUND OF THE INVENTION

Of interest to applications in the biopharmaceutical industry are not only sterile end-products for administration, but also sterile materials used in the production of active pharmaceutical ingredients. Here, materials refer to components of the individual process steps and to media. For example, in the production of monoclonal antibodies, even the fermentation step requires a sterile fermentation vessel and sterile media in order to absolutely ensure an appropriate growth of the cell lines. After cell growth and protein biosynthesis, the antibody must be separated in purest possible form from cells and other undesired components. A wide variety of different process steps are used here. After cell removal by depth filtration or centrigation, these generally include a wide variety of different chromatography steps for the concentration and purification of the target molecule, methods for virus removal and also concentration and sterile-filtration steps. During these process steps too, it is advantageous for the operations to be pathogen-free. This can accordingly minimize the risk of contamination of the final product.

A special case is the cleanup of relatively large molecules such as, for example, viruses or virus-like particles: in many cases, sterile-filtration in the work-up is not possible here. Owing to the size of the molecule, sterile filters that are used would retain the product via their pore size and make a filtration procedure impossible. Here in particular, sterile process solutions are a crucial improvement.

In many of the process steps mentioned, it is standard to lower the risk of a contamination by rinsing with alkaline solution or the use of heat. However, these methods have various disadvantages: in many cases, the implementation in the process is complicated. Large amounts of alkaline solution or else hot steam must be provided. A time-consuming cleaning procedure must be carried out before the actual process step. A further disadvantage is, in many cases, the stability of the materials used in the individual process steps. For example, hot steam cannot be used for sterilizing chromatography media. Other materials do not have sufficient stability with respect to alkaline solution.

In recent years, the trend towards using "single-use" products in the production of active biopharmaceutical ingredients has increased. The single use and predominant use of plastics for materials such as filtration devices thus also paved the way to alternative sterilization methods. Besides autoclaving, sterilization methods such as gas treatment with ethylene oxide or gamma irradiation are used. A further advantage arises here for the user also in the availability of pre-sterilized products for the production process. Thus, cleaning efforts for the user can be reduced or completely dropped.

In general, sterilization methods can be divided into chemical and physical methods. In the case of chemical methods, the use of pathogen-eliminating gases is widespread. However, in this method, it must be ensured that all regions of the material come into sufficient contact with the gas during the sterilization. Physical methods are heat-sterilization and irradiation. In this case, the sterilizing action of the irradiation is based on the destruction of organic material by bond cleavage. The advantage of an irradiation procedure is that all regions of a material can be penetrated.

Chromatography media are customarily sanitized. Sanitization refers to, inter alia, the pathogen-reducing treatment with alkaline solution. In many cases, this involves using a solution of up to 1 molar. However, in this connection, this treatment does not result in a sterile product or a sterile process step. Furthermore, a major disadvantage of this treatment method is the manner of provision. Either the effort in relation to the sanitization must be expended directly before the use in the process, or the manufacturer of the chromatographic medium must sanitize the medium in appropriate chromatography devices as early as during production and supply it in the wet state. This complicates not only the handling; it is also necessary to carry out complex studies in relation to the stability in the storage solution. Pre-sanitized products in chromatography are known as "ready-to-use" products.

It is also possible to use autoclaving for sterilization. This involves having to heat the chromatography medium to at least 121° C. However, this method is unsuitable for relatively large scales, since there is no possibility of implementation for the devices owing to the size.

A further method which has been described is the use of hot buffers for sterilization. This involves heating the chromatography medium likewise to at least 121° C. However, a prerequisite therefor is that the chromatography system is stable with respect to a thermal stress and pressure. This method is not suitable for single-use systems.

US 2013/0062267 A1 describes a sterilization method for providing aseptic chromatography columns. However, this involves having to sterilize the medium and the filtration device (chromatography housing) separately and then introducing the chromatography medium with sterilized equipment into the device. Furthermore, the method is only applicable for polymer gels.

Although already sterile single-use fermentation vessels and filtration devices have become established in the area of filtration and fermentation, it has so far not yet been possible for readily available sterilized products to become established in the application of chromatography. A major reason therefor is the stability of the materials. In this connection, both support matrix and ligand can be damaged by influence of heat, gamma irradiation or other sterilization methods or they are only insufficiently accessible. In chromatography, the support matrices used are, for example, polymer gels, membranes, non-wovens, films or fibres. Ligands can be, inter alia: proteins, substrates, carboxymethyl, sulfonates, quaternary amines, aminoethyl, metal chelates or hydrophobic groups. In this connection, the irradiation of the materials can, for example, damage or detach the side chains of polymers. A treatment with oxidative media such as with reactive ethylene oxide can similarly lead to an alteration of the ligands.

The sterilization methods known in the prior art demonstrably lead to a change in the material properties, as can be seen directly on discolorations of the chromatography material for example. Although such discolorations need not necessarily be adverse in terms of the production contamination in the process, they may nonetheless be undesired, as described in US 2011/0064608 A1 for example.

SUMMARY OF THE INVENTION

It is therefore an object of the present invention to provide a method for sterilizing a chromatography material, more particularly microporous polymer membranes, which method does not change the material properties of the chromatography material, meaning that the chromatography material can be used for a sterile chromatography procedure.

This object is achieved by the embodiments of the present invention that are characterized in the claims.

In particular, the invention provides a method for sterilizing a chromatography material, comprising the steps:
(a) treating the chromatography material with an aqueous, basically buffered saline solution; and
(c) irradiating the chromatography material treated in step (a) with gamma radiation.

According to a preferred embodiment, the method according to the invention further comprises step (b) between steps (a) and (c) and/or step (d) after step (c):
(b) drying the chromatography material treated in step (a);
(d) drying the chromatography material irradiated in step (c), wherein, when step (b) is carried out, the chromatography material dried in step (b) is irradiated with gamma radiation in step (c).

DESCRIPTION OF THE INVENTION

In the context of the present invention, the term "chromatography material" is understood to mean any material which can be used as stationary phase for chromatographic methods. The chromatographic method involves separating a substance mixture on the basis of interactions between the individual constituents of the substance mixture with the stationary and the mobile phase.

The chromatography material in the method according to the invention is not subject to any special restriction. For example, the chromatography material encompasses membranes, porous, polymeric monolithic shaped articles, polymer gels, films, non-wovens, fibres or fabrics. The method according to the invention is suitable especially for membranes, porous, polymeric monolithic shaped articles, polymer gels, films, non-wovens, fibres and fabrics having outer and/or inner surface(s) which has/have been modified by ligands, such as, for example, proteins, substrates, carboxymethyl, sulfonates, quaternary amines, aminoethyl, metal chelates or hydrophobic groups, since the method according to the invention makes it possible to sterilize the chromatography material without the material properties changing with respect to support matrix and ligand.

According to one embodiment of the present invention, the chromatography material to be sterilized is a polymer membrane, more particularly a (surface-modified) microporous polymer membrane. According to the invention, the term "microporous polymer membrane" is understood to mean a polymer membrane having a pore size of from 0.01 µm to 10 µm. According to the present invention, the membrane can comprise cellulose, cellulose derivatives, polyester, polyethylene (PE), polyamide, polyethersulfone (PES), polyvinylidene difluoride (PVDF), polytetrafluoroethylene (PTFE), polypropylene (PP) and polysulfone as structure-imparting constituent, it being possible for these materials to be used individually or in an appropriate combination.

Microporous polymer membranes for use in chromatographic applications are suitable especially for integration into filtration devices (chromatography housings) by, for example as described in DE 197 11 168 A1, a chromatographic bed being formed from multiple polymer membrane plies arranged in series. In such devices, which are also referred to as membrane adsorbers, at least one ply of a polymer membrane is present as web material, the at least one polymer membrane customarily having a thickness of from 50 µm to 350 µm. Customarily, the at least one polymer membrane has an inner porosity of from 50% to 90%.

According to the present invention, the aforementioned non-wovens as chromatography material can be those comprising cellulose, cellulose ester, polyester and polyamide as structure-imparting constituent, it being possible for these materials to be used individually or in an appropriate combination. According to the invention, individual fibres or multicomponents which structure the non-wovens can be concerned. Said individual fibres or multicomponents can have a diameter of from 50 µm to 500 µm.

According to the invention, the fibres as chromatography material can be those comprising cellulose, cellulose ester, polyester and polyamide as structure-imparting constituent, it being possible for these materials to be used individually or in an appropriate combination. In this connection, the fibres can be smooth or structured with channels, it being possible according to the present invention for the fibres to be nanofibres and/or microfibres having a diameter of from 100 nm to 100 µm.

Moreover, according to the present invention, the aforementioned fabrics as chromatography material can comprise the aforementioned fibres as structure-imparting constituent.

In step (a) of the method according to the invention, the chromatography material to be sterilized is treated with an aqueous, basically buffered saline solution in order to preserve the material for the irradiation step (c) of the method according to the invention. In this connection, the chromatography material can be treated either immediately after its production, i.e. after production of the material and an optionally performed surface modification in which relevant ligands are bonded to the matrix, or else only after storage. According to the invention, the term "treating" is not subject to any special restriction. For example, the chromatography material to be stabilized is admixed with an aqueous, basically buffered saline solution and shaken in the course of this, for example for a period of about 10 minutes, in order to achieve a complete wetting or a complete exchange with the solution present in the pores. In this connection, it is possible according to the present invention for the treatment to be carried out at room temperature or ambient temperature. According to the invention, the chromatography material to be treated is, for example, introduced into the aforementioned solution in an appropriate vessel, said vessel then being placed onto a shaker swiveling at from 30 to 150 rpm. Alternatively, it is also possible according to the invention for the chromatography material to be treated by stirring of the solution in which the chromatography material is situated. In a further embodiment, it is also possible according to the present invention for the chromatography material to be guided through a trough in which the solution is optionally circulated.

Step (a) of the method according to the invention can be carried out either with an isolated chromatography material, i.e. the chromatography material is not situated in a (chromatography) housing, as described above, or with a chromatography material already integrated in a (chromatography) housing, i.e. situated in an integrated state. In the latter case, according to the invention, the aqueous, basically buffered saline solution as treatment solution is appropriately introduced into the housing such that the above-described treatment goals are achieved. For example, the treatment solution can flow through the housing containing the integrated chromatography material. Further explanations in the event of the chromatography material already being integrated into a housing are given below.

According to the invention, the aqueous, basically buffered saline solution that is used in step (a) is not subject to any special restriction.

Buffer solutions contain a mixture of a weak acid and its conjugate or corresponding base (or of the respective salt) or of a weak base and its conjugate or corresponding acid. Ampholytes (bifunctional molecules) can serve as buffers too. The pH-determining factor is the ratio or the protolysis equilibrium of the buffer pair. According to the present invention, fundamentally suitable acid-base pairs are those having a pKa of greater than 4.

The saline solution or buffer solution according to the present invention can comprise one or more salts so long as the buffer solution has a pH greater than 7, preferably greater than 8.

According to the invention, water can be used as solvent for the basically buffered saline solution. In addition, mixtures are also possible, such as, for example, a mixture of water and glycerol. Fundamentally suitable are solvents by means of which relevant saline solutions or buffer solutions can be prepared according to the present invention, while the chromatography material to be treated is inert with respect to such solvents.

According to a preferred embodiment, the saline solution in step (a) comprises at least one salt selected from the group consisting of sodium acetate, sodium dihydrogen phosphate, disodium hydrogen phosphate, trisodium phosphate, sodium dihydrogen citrate, disodium hydrogen citrate and trisodium citrate. According to a preferred embodiment of the present invention, the saline solution in step (a) comprises disodium hydrogen phosphate. The salt concentration of the saline solution in step (a) is preferably from 0.01 to 1 mol/L, particularly preferably from 0.02 to 0.1 mol/L. In the case of a salt concentration of below 0.01 mol/L, it is not possible to rule out in the subsequent irradiation that a change in the treated chromatography material will not occur owing to the action of the radiation. Moreover, in the case of a salt concentration of above 1 mol/L, it is not possible to rule out that the chromatography material will not already be damaged by the treatment solution itself and/or be subject to an undesired change.

According to a preferred embodiment, the aqueous, basically buffered saline solution in step (a) further comprises from 10 to 40% by weight of glycerol. This is especially advantageous when the chromatography material is a porous polymer membrane, since in this case the glycerol protects the fine porous membrane structure during the drying steps (b) and (d).

In step (c) of the method according to the invention, the chromatography material treated in step (a) is irradiated with gamma radiation in order to sterilize the chromatography material. Advantageously, the performed preservation step (a) of the method according to the invention means that the material properties of the chromatography material do not change as a result of the gamma irradiation, as is the case for irradiation of untreated chromatography materials known in the prior art, i.e. for materials which have not undergone preservation step (a). According to the present invention, the irradiation is, for example, effected using a cobalt source or using electron beams having an energy of from 1 to 12 MeV. In this connection, the material to be irradiated is, for example, conveyed on conveyor belts around the radiation source. In this case, the number of passes depends on the desired minimum dose, which is customarily monitored. According to the invention, such an irradiation procedure can be carried out in room air or under a protective atmosphere. According to a preferred embodiment, irradiation is carried out in step (c) with a gamma radiation dose of from 1 kGy to 100 kGy. In the case of a radiation dose of less than 1 kGy, there is the risk of the chromatography material being insufficiently sterilized. In the case of a radiation dose of more than 100 kGy, the irradiated materials may be damaged; more particularly, they may lose their strength and become brittle. Particularly preferably, irradiation is carried out in step (c) with a radiation dose of from 15 kGy to 85 kGy, in particular from 30 kGy to 70 kGy.

As already explained above, the method according to the invention further preferably comprises step (b) between steps (a) and (c) and/or step (d) after step (c):
(b) drying the chromatography material treated in step (a);
(d) drying the chromatography material irradiated in step (c), wherein, when step (b) is carried out, the chromatography material dried in step (b) is irradiated with gamma radiation in step (c).

In step (b) and/or in step (d) of the method according to the invention, the chromatography material treated in step (a) or the chromatography material irradiated in step (c) is dried. According to the invention, the term "drying" is not subject to any special restriction. For example, the drying in step (b) and/or in step (d) can be done at room temperature or else at elevated temperature, for example in an oven. In addition or as an alternative, the drying can be done according to the present invention by blowing dry inert gases onto or through the chromatography materials treated in step (a) and/or the chromatography materials irradiated in step (c). According to a preferred embodiment of the present invention, the chromatography material is dried in step (b) and/or in step (d) at a temperature of from 70° C. to 90° C. for a period of from 5 min to 20 min.

If the aqueous, basically buffered saline solution comprises glycerol as described above in a preferred embodiment, this can cause a residual moisture after the drying. According to the invention, this can remain in the treated chromatography material. Alternatively, according to the present invention, such a residual moisture can be further reduced or removed by carrying out both step (b) and step (d).

According to one embodiment of the method according to the invention, the chromatography material is enclosed in a sterile, irradiatable item of packaging after step (a) or after step (b) and then irradiated with gamma radiation in said item of packaging. As a result, the gamma radiation-sterilized chromatography material can advantageously be stored and transported in a sterile state without there being the risk of a subsequent contamination following irradiation. Such sterile, irradiatable items of packaging are known to a person skilled in the art and are, for example, commercially available under the registered trade name Tyvek® from DuPont.

For example, an end product, for example as a closed system having sterile connectors, is introduced into a suitable item of packaging such as, for example, pouch and cardboard packaging and then irradiated while thus packaged. In this connection, it is possible according to the present invention for both individual items of cardboard packaging and arrangements thereof on pallets to be subjected to an irradiation procedure.

According to a further embodiment of the present invention, the chromatography material is, at least when carrying out step (c) of the method, situated and already integrated in a housing. In this connection, it is possible according to a preferred embodiment in accordance with the invention for the housing to be already introduced into an irradiatable item of packaging.

Moreover, it is also possible according to the invention for the chromatography material to be already integrated into a housing while carrying out the entire method, i.e. when carrying out steps (a) (as already described above), optionally (b), (c) and optionally (d). In this connection, it is either unnecessary to dry the chromatography material for an end use thereof, or the embodiment of the housing allows steps (b) and/or (d) in the form of, for example, application of heat and/or of the blowing or blow-through of appropriate gases.

Furthermore, the present invention provides a chromatography material which has been sterilized by the method according to the invention. The chromatography material sterilized according to the invention can advantageously be used for the chromatographic removal of contaminants from a fluid under sterile conditions. Such chromatographic removal methods are known to a person skilled in the art.

Lastly, the present invention provides a closed, chromatographic filtration system comprising a sterile filtration device comprising a chromatography material sterilized according to the invention, assembled sterile hoses and sterile connections. Such filtration systems without the chromatography material sterilized according to the invention are known to a person skilled in the art.

Advantageously, the method of the present invention makes it possible to sterilize a chromatography material, more particularly (surface-modified) microporous polymer membranes, without the material properties of the chromatography material changing. After sterilization, the chromatography material sterilized according to the invention can advantageously be stored without discolouring. Since the adsorption capacity of the chromatography material advantageously does not change as a result of the sterilization according to the invention, the chromatography material sterilized according to the invention can be used especially for the chromatographic removal of contaminants from a fluid under sterile conditions.

The present invention will be more particularly elucidated on the basis of the following, non-restrictive examples.

EXAMPLES

Comparative Example

Type 1 to 3 membrane adsorbers wetted with water were treated at room temperature for 10 min with an aqueous glycerol solution having a proportion of 30% by weight of glycerol with shaking and then dried in a drying cabinet at 80° C. for 10 minutes.
Type 1: MA Sartobind® S from Sartorius Stedim Biotech GmbH, commercially available
Type 2: MA Sartobind® HIC Phenyl from Sartorius Stedim Biotech GmbH, commercially available
Type 3: Membrane, produced in accordance with DE 10 2013 017 014 from Sartorius Stedim Biotech GmbH
Sterilization Method According to the Invention:

The type 1 to 3 membrane adsorbers wetted with water were treated as in the comparative example, with the glycerol solution having a proportion of 30% by weight of glycerol additionally containing 1% by weight of a salt (sodium acetate trihydrate or disodium hydrogen phosphate dihydrate or trisodium citrate trihydrate).

Exemplary Embodiment 1: Discoloration in the Sterilization of Membrane Adsorbers The discoloration following gamma irradiation with a dose of at least 50 kGy (minimum measured surface dose 50.7 kGy, maximum measured surface dose 55.8 kGy) was determined by subjecting rectangular cuts of membrane adsorbers to a stability study. To this end, accelerated ageing was carried out under controlled conditions (40° C.±2° C., 75%±5% relative air humidity) after the irradiation for membrane cuts of membranes which were treated with an aqueous, basically buffered saline solution (designations in the figures: "Acetate", "Phosphate", "Sodium citrate") and of membranes which were not exposed to the treatment step according to the invention (designation in the figures: "Standard"). According to the invention, every 100 days of storage under the chosen accelerated ageing conditions correspond to about 1.5 years of storage under standard conditions. Under the same accelerated ageing conditions, ageing was also carried out for a membrane cut of a membrane which was first sterilized with use of ethylene oxide (designation in the figures: "EtO"), i.e. was treated at first with ethylene oxide, and was then exposed to the above-described gamma irradiation.

After rinsing, the cuts were shrink-wrapped in gamma stable plastics bags and stored. After defined intervals of time (0, 100, 200 days), samples of the membrane were removed and examined.

FIG. 1 shows the optical appearance of the respective membranes after 0, 100 and 200 days.

The ageing study shows that, over a period of at least 200 days, the optical appearance of the membrane adsorbers sterilized according to the invention advantageously remains stable in comparison with a sterilized membrane adsorber without preceding application of the treatment step (a) according to the invention, i.e. changes in the material properties in the form of discolorations did not occur.

Exemplary Embodiment 2: Influence on the Adsorption Capacity

The method according to the invention was used to rinse and sterilize a cation-exchange membrane based on stabilized cellulose of the type MA Sartobind®, commercially available from Sartorius Stedim Biotech GmbH, under the above-stated conditions (see "Sterilization method according to the invention" and "Exemplary embodiment 1").

Thereafter, the binding capacity was ascertained as follows: 1 g/L lysozyme were dissolved in phosphate buffer (buffer constituents potassium hydrogen phosphate and dipotassium hydrogen phosphate) having a molarity of 10 mM and a pH of 7.0. Three 5 cm² plies of the membrane adsorber were integrated into a filtration housing and connected to a chromatography system (Äkta Explorer, GE Healthcare). Before the loading with the protein solution, the adsorber was equilibrated with 20 mL of a 10 mM phosphate buffer, pH 7 at 10 mL/min.

The dynamic capacity was determined on the chromatography system Äkta Explorer from GE Healthcare by means of an absorption measurement at 280 nm using a UV-VIS photometer. The concentration was calculated from the measured absorbance according to the Beer-Lambert law. The extinction coefficient for lysozyme was determined at $2.47*10^{-3}$ L/(g*cm).

The binding capacity was determined for the time at which 10% of the concentration of the starting solution was measured at the output of the filtration housing.

$$Cap_{10\%} = \frac{(V_{10\%} - V_{dead})*A(SS)}{\varepsilon*d*A_{membrane}}$$

$Cap_{10\%}$: Dynamic capacity, 10% [mg/cm$^2$]
$V_{10\%}$: Loaded volume of the starting solution upon breakthrough of 10% of the concentration of the starting solution [L]
$V_{dead}$: Dead volume of the chromatography system [L]
A(SS): Absorbance of the starting solution
$\varepsilon$: Specific extinction coefficient=$2.47*10^{-3}$ [L/(mg*cm)]
d: UV measurement layer thickness=1 [cm]
$A_{membrane}$: Membrane area [cm$^2$]

FIG. 2 shows the influence of the method steps according to the invention on the relevant adsorption properties of the membrane.

As can be clearly seen from FIG. 2, the method according to the invention (irradiation with a dose of at least 50 kGy after rinsing step according to the invention) advantageously does not significantly impair the adsorption capacity of the membrane in comparison with non-sterilized membrane adsorbers, i.e. the sterilization method according to the invention advantageously did not change the material properties of the chromatography material. By contrast, membranes which were irradiated in the absence of rinsing step according to the invention show a decrease in the adsorption capacity owing to changes in the material properties.

DESCRIPTION OF THE DRAWINGS

The Figures Show.

Figure 1A:
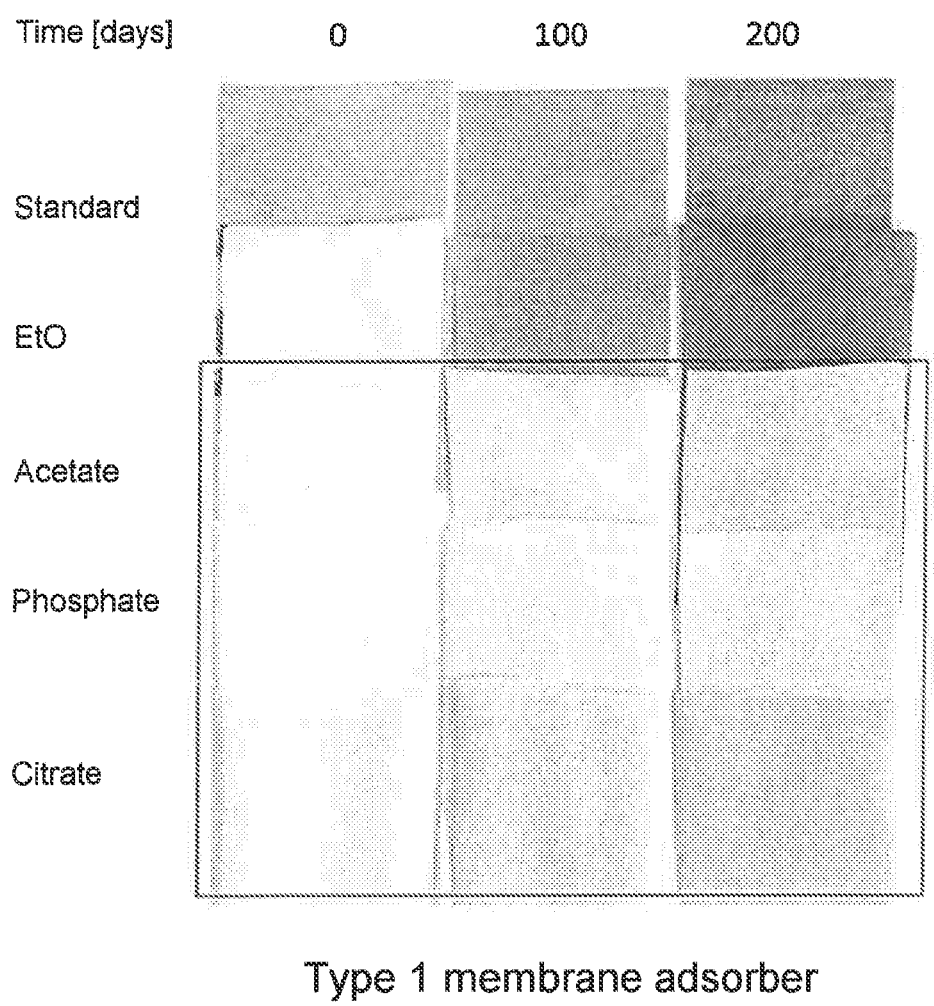
FIG. 1: Optical appearance of membranes with and without performed sterilization method according to the invention, after defined ageing periods (0, 100 and 200 days).
Figure 1B:
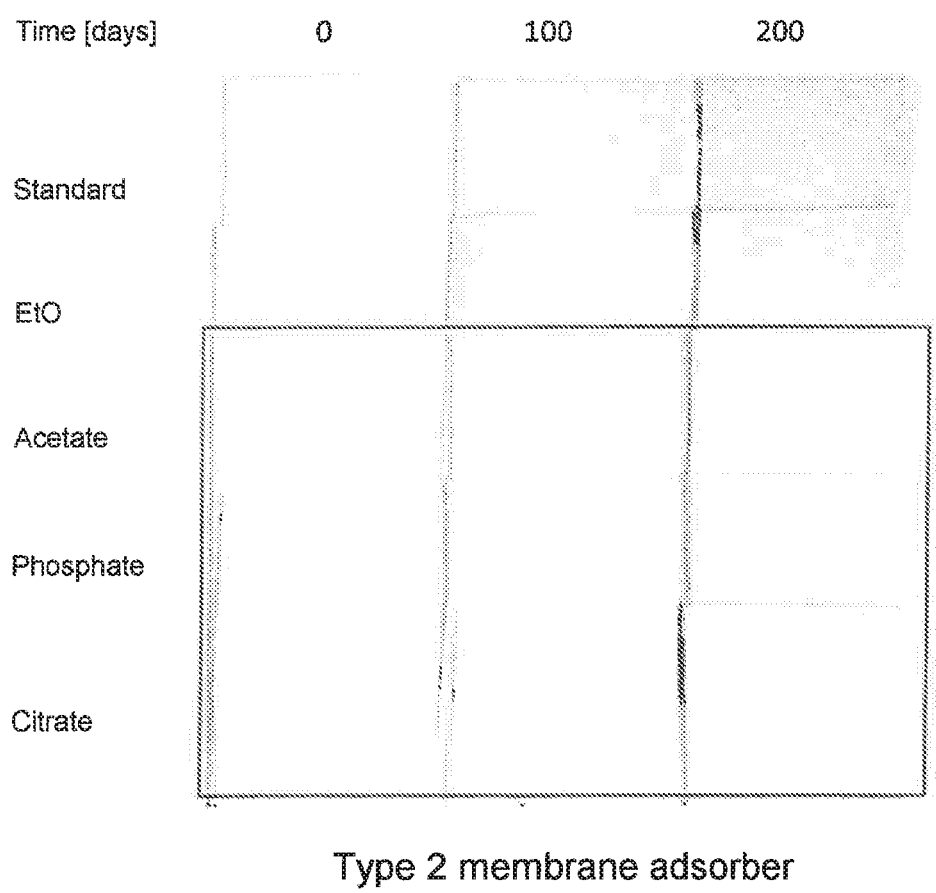
Figure 1C:
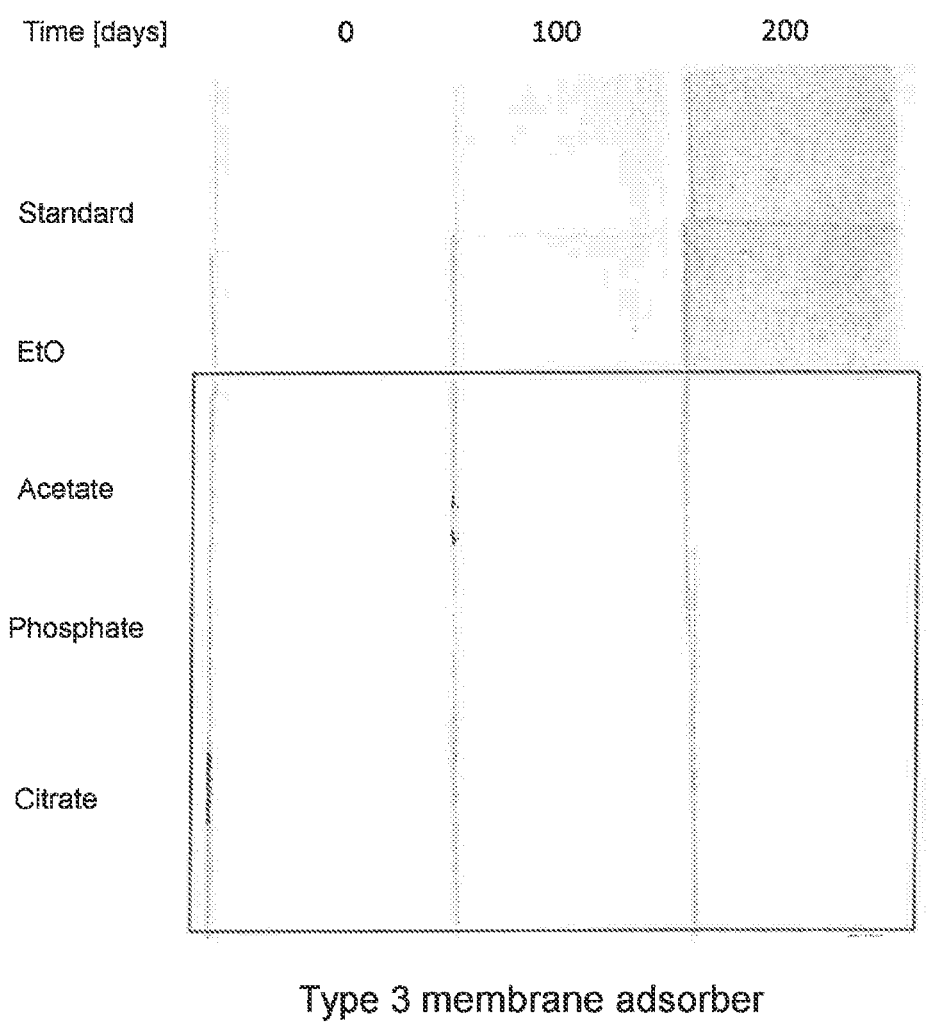
Figure 2:
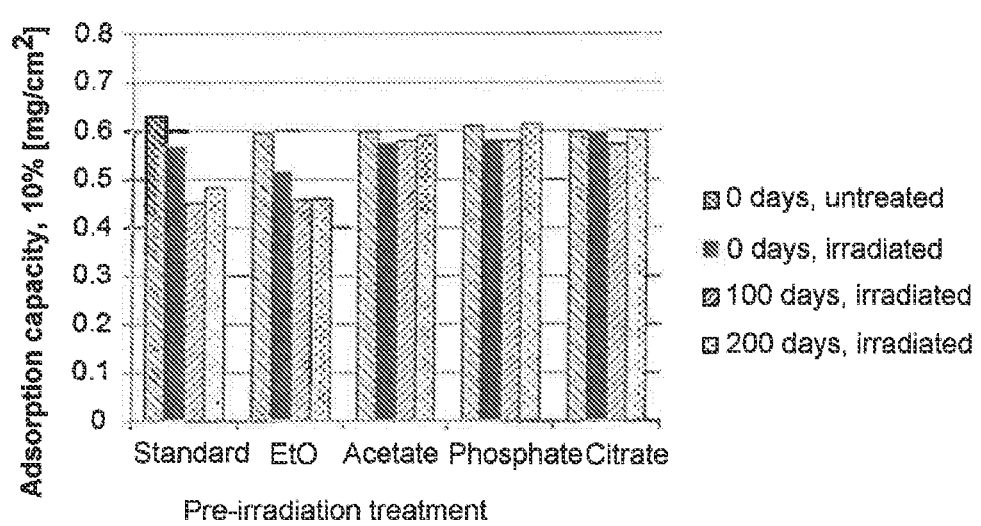
FIG. 2: Comparison of the adsorption properties of membranes with and without performed sterilization method according to the invention.

The invention claimed is:
1. Method for sterilizing a chromatography material, comprising the steps:
(a) treating the chromatography material with an aqueous, basically buffered saline solution; and
(c) irradiating the chromatography material treated in step (a) with gamma radiation.
2. Method according to claim 1, further comprising step (h) between steps (a) and (c) and/or step (d) after step (c):
(b) drying the chromatography material treated in step (a);
(d) drying the chromatography material irradiated in step (c);
wherein the chromatography material dried in step (b) is irradiated with gamma radiation in step (c).
3. Method according to claim 2, wherein the chromatography material is dried up in step (b) and/or in step (d) in a temperature range of from 70° C. to 90° C. for a period of from 5 min to 20 min.
4. Method according to claim 1, wherein the chromatography material is selected from membranes, porous, polymeric monolithic shaped articles, polymer gels, films, nonwovens, fibres and fabrics.
5. Method according to claim 1, wherein the chromatography material is a microporous polymer membrane.
6. Method according to claim 5, wherein the microporous polymer membrane has a thickness of from 50 to 350 µm.
7. Method according to claim 1, wherein the aqueous, basically buffered saline solution in step (a) comprises at least one salt selected from the group consisting of sodium acetate, sodium dihydrogen phosphate, disodium hydrogen phosphate, trisodium phosphate, sodium dihydrogen citrate, disodium hydrogen citrate and trisodium citrate.
8. Method according to claim 1, wherein the salt concentration of the saline solution in step (a) is from 0.01 to 1 mol/L.
9. Method according to claim 1, wherein the aqueous, basically buffered saline solution in step (a) further comprises from 10 to 40% by weight of glycerol.
10. Method according to claim 1, wherein irradiation is carried out in step (c) with a gamma radiation dose of from 1 kGy to 100 kGy.
11. Method according to claim 1, wherein the chromatography material is, when carrying out the method, situated and integrated in a housing.
12. Method according to claim 11, wherein the housing containing the integrated chromatography material is situated in an irradiatable item of packaging in step (c).
13. Method according to claim 1, wherein the chromatography material is situated in an irradiatable item of packaging in step (c).
14. Chromatography material which has been sterilized by a method comprising the steps:
(a) treating the chromatography material with an aqueous, basically buffered saline solution; and
(c) irradiating the chromatography material treated in step (a) with gamma radiation.
15. Use of a chromatography material sterilized by a method comprising the steps:
(a) treating the chromatography material with an aqueous, basically buffered saline solution:
(c) irradiating the chromatography material treated in step (a) with gamma radiation to give a sterilized chromatography material; and
using the sterilized chromatography material for the chromatographic removal of contaminates from a fluid.
16. Closed chromatographic filtration system comprising a sterile filtration device comprising a chromatography material sterilized by treating the chromatography material with an aqueous, basically buffered saline solution to give a treated chromatography material; and irradiating the treated chromatography material with gamma radiation,
assembled sterile hoses; and
sterile connections.

* * * * *